United States Patent [19]

Larock

[11] Patent Number: 4,992,568

[45] Date of Patent: Feb. 12, 1991

[54] SYNTHESIS OF BENZOFURANS

[75] Inventor: Richard C. Larock, Ames, Iowa

[73] Assignee: Iowa State University Research Foundation, Inc., Ames, Iowa

[21] Appl. No.: 398,622

[22] Filed: Aug. 25, 1989

[51] Int. Cl.$^5$ .................................... C07D 307/79
[52] U.S. Cl. .................................................. 549/476
[58] Field of Search ........................................ 549/471

[56]  References Cited
U.S. PATENT DOCUMENTS 3,705,919  12/1972  Heck ................................. 549/471

OTHER PUBLICATIONS

Larock et al., Tet. Letters, 29(37), pp. 4687–4690 (Sep. 1988).
Mori et al., Tet. Letters, No. 12, pp. 1037–1040 (1977).
Ames et al., Tetrahedron, 40(10), pp. 1919–1925 (1984).

Primary Examiner—Mary C. Lee
Assistant Examiner—Bernard I. Dentz
Attorney, Agent, or Firm—Zarley McKee, Thomte, Voorhees & Sease

[57]  ABSTRACT o-Iodoaryl allyl ethers undergo facile palladium-promoted cyclization to benzofurans.

10 Claims, No Drawings

SYNTHESIS OF BENZOFURANS

GRANT REFERENCE

The invention described herein was made in part in the course of work under a grant from the National Institute of Health, No. GM-24254.

BACKGROUND OF THE INVENTION

This invention relates to a one pot synthesis of benzofurans. The simplest benzofuran has the empirical formula $C_8H_6O$, and is also from time to time referred to as coumarone. It is a bicyclic ring compound derived from coal-tar naptha and is the parent substance of coumarone-indene resins. It has the following structure:

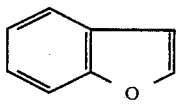

These coumarone or benzofuran compounds are known to be useful for a wide variety of purposes. Amongst those are use in the perfume industry, in agriculture and horticulture as growth enhancers, and in some instances some of the coumarones are known to be physiologically active.

Past processes have involved complex multi-step synthesis to afford relatively low yields of compound. Thus, for the most part, industrial preparation of these as pure compounds has not been without difficulty.

It therefore can be seen that there is a continuing need for the development of processes, particularly one-step processes of preparing benzofurans so that they may be conveniently used for their known purposes.

It is a primary objective of the present invention to fulfill this need by an improved one-pot process for the preparation of benzofurans.

It is a further object of the present invention to prepare 3-methyl benzofuran.

The method and manner of accomplishing each of the above objectives, as well as others, will become apparent from the detailed description of the invention which follows.

SUMMARY OF THE INVENTION

A one-step method of preparing benzofurans, particularly 3-methyl benzofuran. The process comprises cyclizing an ortho-iodoaryl allyl ether in the presence of a palladium catalyst to yield a 3-substituted benzofuran.

DETAILED DESCRIPTION OF THE INVENTION

In accordance with this invention, ortho-iodoaryl allyl ethers are cyclized to benzofurans. The reaction is represented by the following equation:

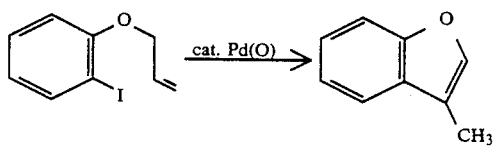

The starting compound of the present invention is an ortho-iodoaryl allyl ether, particularly ortho-iodophenyl allyl ether. It is conceivable that the bromo-compounds could be utilized as opposed to the iodo-compounds, but it is believed that bromo-compounds would require significantly elevated temperatures from those hereinafter expressed. Thus, iodo-compounds are specifically utilized in the examples hereinafter.

The reaction may be run in the presence of polar solvents, such as dimethylformamide (DMF); acetonitrile; and dimethyl sulfoxide (DMSO). The precise polar solvent is noncritical. It simply need be a suitable solvent for ortho-iodophenyl allyl ether.

The reaction may be run at temperatures of from about 60° C. to about 120° C., preferably from about 70° C. to about 100° C. The reaction time may be from 0.5 days up to 2 days, preferably a one day reaction time.

As can be seen from the general equation, the reaction occurs in the presence of a palladium catalyst, the catalyst being introduced as either a Pd(II) salt, such as palladium acetate, palladium halide or palladium nitrate, most preferably palladium acetate, or as a palladium(0) reagent, such as $Pd(PPh_3)_4$ or $Pd(dba)_2$ (dba=dibenzylidene acetone). While the exact mechanism is not known, it is believed that some of the palladium(II) salt is reduced to a palladium(0) catalyst which is the active form and that this palladium(0) inserts into the carbon halogen bond. The arylpalladium compound thus generated adds to the carbon-carbon double and eventually eliminates a palladium hydride to generate the benzofuran. However, it is to be emphasized that applicants do not wish to be bound by a mechanistic description of the reaction, simply instead preferring to describe the reaction that does occur without limitation to any particular theory.

It can be seen from the above reaction that it is essential that the reaction be conducted in the presence of a palladium salt, preferably palladium acetate. While not important for describing the overall process, the believed reason for the essential nature of the palladium salt is that the palladium salt is necessary for the cyclization. The scheme by which it is believed this occurs is disclosed in a paper on the same topic, Larock, et al. *Tetrahedron Letters*, 29, 4687 (1988) at page 4688, which is incorporated herein by reference. Basically during the process, the palladium(II) is reduced to palladium(0), which then promotes intramolecular cyclization.

For reasons that are not precisely known, it has been found that the reaction functions most effectively in a slightly basic environment, as represented by an inorganic base such as sodium carbonate. Other bases such as bicarbonate, acetate or organic amine bases can also be employed, but sodium carbonate is the base of choice. The amount can be one equivalent or more per each equivalent of ortho-iodoaryl allyl ether.

Tetra-n-butylammonium chloride is also important to the reaction. Its role is not clear except that it increases the rate of reaction. Other quarternary ammonium or phosphonium salts can also be used. The presence of a formate salt also seems to increase the yield somewhat. A number of different formate salts can be used.

The following examples are offered to illustrate and not limit the process of this invention.

In all of the examples, the reaction procedure was basically the same, except for the change in the substrate, i.e., the precise ortho-iodoaryl allyl ether used to commence the process labeled in the table below as "substrate". All reactions were stirred in a 1 dram vial at 80° C. for two days using 5% palladium acetate (0.015 mmol), sodium carbonate (0.75 mmol), $NaO_2CH$ (0.3 mmol), substrate (0.3 mmol), DMF (0.6 ml), and tetra-n-butylammonium chloride (0.33 mmol). All products gave appropriate proton and $^{13}C$ NMR, IR and mass spectral data.

TABLE I

Synthesis of Benzofurans via o-Iodoaryl Allyl Ethers

| Entry | Substrate | Benzofuran | Isolated Yield (%) |
|---|---|---|---|
| 1 | | | 47 |
| 2 | | | 83 |
| 3 | | | 83 |
| 4 | | | 45, 81 |
| 5 | | | 76 |
| 6 | | | 52 |
| 7 | | | 40 |
| 8 | | | 42 |

What is claimed is:

1. A one step method of preparing benzofurans, comprising: cyclizing an o-iodoaryl allyl ether in the presence of a palladium catalyst to yield a 3-substituted benzofuran.

2. The method of claim 1 wherein the ether is o-iodophenyl allyl ether.

3. The method of claim 1 wherein the reaction is run at elevated temperatures.

4. The method of claim 3 wherein the reaction is run at a temperature within the range of about 60° C. to about 120° C.

5. The method of claim 4 wherein the reaction is run at a temperature within the range of 70° C. to about 100° C.

6. The method of claim 1 wherein the reaction is run in the presence of a polar solvent.

7. The reaction of claim 1 wherein the reaction is run in the presence of a base.

8. The reaction of claim 7 wherein the base is inorganic.

9. The reaction of claim 7 wherein the base is organic.

10. The reaction of claim 7 wherein the reaction is run in the presence of tetra-n-butylammonium chloride.

* * * * *